(12) United States Patent  
Yamamoto

(10) Patent No.: US 11,510,599 B2
(45) Date of Patent: Nov. 29, 2022

(54) ENDOSCOPE SYSTEM, PROCESSOR DEVICE, AND METHOD OF OPERATING ENDOSCOPE SYSTEM FOR DISCRIMINATING A REGION OF AN OBSERVATION TARGET

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 669 days.

(21) Appl. No.: 16/546,726

(22) Filed: Aug. 21, 2019

(65) Prior Publication Data

US 2019/0374141 A1    Dec. 12, 2019

Related U.S. Application Data

(63) Continuation of application No. PCT/JP2018/006473, filed on Feb. 22, 2018.

(30) Foreign Application Priority Data

Feb. 24, 2017    (JP) .............................. JP2017-033980

(51) Int. Cl.
*A61B 5/1455*  (2006.01)
*A61B 1/05*    (2006.01)
(Continued)

(52) U.S. Cl.
CPC ........ *A61B 5/14552* (2013.01); *A61B 1/0005* (2013.01); *A61B 1/00186* (2013.01);
(Continued)

(58) Field of Classification Search
None
See application file for complete search history.

(56) References Cited

U.S. PATENT DOCUMENTS 5,515,449 A * 5/1996 Tsuruoka ......... A61B 1/000094
348/45
5,956,416 A * 9/1999 Tsuruoka ......... A61B 1/000094
382/128
(Continued)

FOREIGN PATENT DOCUMENTS

EP    2912991 A1    9/2015
EP    2979607 A1    2/2016
(Continued)

OTHER PUBLICATIONS

Japanese Office Action for corresponding Japanese Application No. 2019-501416, dated Apr. 28, 2020.
(Continued)

*Primary Examiner* — John P Leubecker
(74) *Attorney, Agent, or Firm* — Birch, Stewart, Kolasch & Birch, LLP

(57) ABSTRACT

An endoscope system includes a light source unit, an image sensor, an image acquisition unit, a first image generation unit, a second image generation unit, and a region discrimination unit. The light source unit emits a plurality of types of illumination light beams with different wavelengths. The image acquisition unit acquires images corresponding to the respective illumination light beams. The first image generation unit generates a first image (white light image) serving as a base of a display image. The second image generation unit generates a second image (bright/dark region discrimination image or the like), using at least one image having a different corresponding wavelength from that of the image used for the generation of the first image. The region discrimination unit discriminates the regions in the observation target, using the second image.

13 Claims, 9 Drawing Sheets

(51) Int. Cl.
  *A61B 1/06* (2006.01)
  *G06T 5/00* (2006.01)
  *G06T 7/00* (2017.01)
  *H04N 9/04* (2006.01)
  *A61B 1/00* (2006.01)
  *A61B 5/00* (2006.01)
  *H04N 5/235* (2006.01)
  *H04N 5/225* (2006.01)

(52) U.S. Cl.
  CPC .............. *A61B 1/05* (2013.01); *A61B 1/0638* (2013.01); *A61B 5/489* (2013.01); *G06T 5/001* (2013.01); *G06T 7/0014* (2013.01); *H04N 5/2354* (2013.01); *H04N 9/0451* (2018.08); *G06T 2207/10068* (2013.01); *G06T 2207/10152* (2013.01); *G06T 2207/20004* (2013.01); *G06T 2207/30096* (2013.01); *H04N 2005/2255* (2013.01)

(56) References Cited

U.S. PATENT DOCUMENTS

| | | | |
|---|---|---|---|
| 7,428,333 B2* | 9/2008 | Asari | G06T 5/009 |
| | | | 358/518 |
| 8,472,682 B2* | 6/2013 | Guissin | A61B 5/444 |
| | | | 382/128 |
| 9,161,734 B2 | 10/2015 | Vincent et al. | |
| 9,165,370 B2 | 10/2015 | Hirota et al. | |
| 10,194,783 B2 | 2/2019 | Kono et al. | |
| 10,891,743 B2* | 1/2021 | Hirota | G06F 9/30003 |
| 2010/0049058 A1 | 2/2010 | Ishihara | |
| 2011/0237915 A1* | 9/2011 | Yamaguchi | A61B 1/0655 |
| | | | 600/339 |
| 2012/0220840 A1* | 8/2012 | Morita | A61B 1/000094 |
| | | | 600/109 |
| 2012/0327205 A1* | 12/2012 | Takahashi | G02B 23/2476 |
| | | | 348/65 |
| 2013/0002844 A1 | 1/2013 | Shida | |
| 2014/0024948 A1* | 1/2014 | Shida | A61B 1/043 |
| | | | 600/476 |
| 2014/0037179 A1* | 2/2014 | Shida | A61B 1/00055 |
| | | | 382/132 |
| 2014/0085686 A1* | 3/2014 | Ishihara | A61B 1/000094 |
| | | | 358/475 |
| 2014/0221744 A1* | 8/2014 | Yamaguchi | A61B 1/05 |
| | | | 600/109 |
| 2014/0221745 A1* | 8/2014 | Yamaguchi | G06T 7/11 |
| | | | 600/109 |
| 2015/0257635 A1* | 9/2015 | Kubo | A61B 1/000094 |
| | | | 600/109 |
| 2015/0320296 A1 | 11/2015 | Morita | |
| 2016/0239965 A1* | 8/2016 | Kuramoto | A61B 5/0059 |
| 2017/0112355 A1 | 4/2017 | Hirota et al. | |
| 2018/0146847 A1 | 5/2018 | Otsuka | |
| 2018/0289246 A1* | 10/2018 | Tabata | A61B 1/044 |

FOREIGN PATENT DOCUMENTS

| | | |
|---|---|---|
| JP | 2008-154846 A | 7/2008 |
| JP | 2010-172673 A | 8/2010 |
| JP | 2012-192051 A | 10/2012 |
| JP | 2015-198735 A | 11/2015 |
| JP | 2016-16185 A | 2/2016 |
| JP | 2016-19665 A | 2/2016 |
| JP | 5854561 B2 | 2/2016 |
| JP | 2016-77756 A | 5/2016 |
| JP | 2016-131837 A | 7/2016 |
| WO | WO 2017/010013 A1 | 1/2017 |

OTHER PUBLICATIONS

Chinese Office Action and Search Report for corresponding Chinese Application No. 201880013789.0, dated Apr. 6, 2021, with English translation of the Office Action.
International Preliminary Report on Patentability (Form PCT/IPEA/409) for International Application No. PCT/JP2018/006473, dated Jun. 21, 2019, with English translation.
International Search Report and Written Opinion of the International Searching Authority (Forms PCT/ISA/210 and PCT/ISA/237) for International Application No. PCT/JP2018/006473, dated May 15, 2018, with English translation of the Search Report.
Chinese Office Action for corresponding Chinese Application No. 201880013789.0, dated Oct. 22, 2021, with an English translation.
Extended European Search Report for corresponding European Application No. 18757449.6, dated Feb. 13, 2020.

* cited by examiner

| | ILLUMINATION LIGHT | IMAGE TO ACQUIRE |
|---|---|---|
| FIRST FRAME | WHITE LIGHT | B1, G1, R1 |
| SECOND FRAME | NARROWBAND PURPLE LIGHT | B2, G2, R2 |
| THIRD FRAME | SECOND NARROWBAND BLUE LIGHT | B3, G3, R3 |
| FOURTH FRAME | NARROWBAND MIXED LIGHT | B4, G4, R4 |

ENDOSCOPE SYSTEM, PROCESSOR DEVICE, AND METHOD OF OPERATING ENDOSCOPE SYSTEM FOR DISCRIMINATING A REGION OF AN OBSERVATION TARGET

CROSS-REFERENCE TO RELATED APPLICATIONS

This application is a Continuation of PCT International Application No. PCT/JP2018/006473 filed on 22 Feb. 2018, which claims priority under 35 U.S.C § 119(a) to Japanese Patent Application No. 2017-033980 filed on 24 Feb. 2017. The above application is hereby expressly incorporated by reference, in its entirety, into the present application.

BACKGROUND OF THE INVENTION

1. Field of the Invention

The present invention relates to an endoscope system, a processor device, and a method of operating an endoscope system that discriminate some regions of an observation target.

2. Description of the Related Art

In the medical field, it is general to perform diagnosis, using endoscopic systems including a light source device, an endoscope, and a processor device. Particularly, in recent years, endoscope systems that discriminate some regions of an observation target are known. For example, endoscope systems described in JP2016-019665A (corresponding to U.S. Pat. No. 10,194,783B2), JP2016-016185A (corresponding to US2017/112355A1), and JP2012-192051A (corresponding to U.S. Pat. No. 9,165,370B2) discriminates regions on which mucous membrane profiles, dark parts, specular reflection, bubbles, or residues are reflected.

Additionally, an endoscope system, which switches observation modes in conformity with the features or the like of the regions to observe, is known (JP2016-131837A). In addition, in medical images, such as a computed tomography (CT) image, it is known that regions are discriminated on the basis of the shape of a histogram showing the frequency of appearance of pixel values for every region (JP5854561B (corresponding to U.S. Pat. No. 9,161,734B2)).

SUMMARY OF THE INVENTION

Discriminating (hereinafter referred to as region discrimination) regions having specific features in endoscope images have been performed from the past. However, depending on the features of regions to discriminate, the situations of observation targets, or the like, robustness may be low, and the regions may be erroneously discriminated. For example, in a case where an attempt to discriminate a region with a residual liquid is made in order to distinguish a mucous membrane and the residual liquid from each other, the discrimination is difficult and a region with the residual liquid cannot be correctly discriminated, in a case where the residual liquid is thin, or the profile of a discriminated region may be inaccurate even in a case where the region with the residual liquid can be discriminated to some extent. In a case where a histogram is used for the region discrimination, more accurate results than discrimination methods for other regions are easily obtained. However, even in the region discrimination using the histogram, the region discrimination of distinguishing the mucous membrane and the residual liquid as described above may be difficult, which may lead to inaccurate results.

Additionally, in a case where an observation mode in which tissue or structure having specific features or the like can be enhanced and observed is prepared, the discrimination accuracy of a region having the tissue, structure, or the like having the specific features or structure is improved. However, in a case where an observation mode is provided, the prepared observation mode is basically specialized in identification of one type of specific tissue or structure. Thus, it is difficult to simultaneously and accurately discriminate a plurality of regions having different features from one image acquired and displayed in the prepared observation mode.

An object of the present invention is to provide an endoscope system, a processor device, and a method of operating an endoscope system that can substantially simultaneously and accurately discriminate a plurality of regions having different features.

An endoscope system of the invention comprises a light source unit, an image sensor, an image acquisition unit, a first image generation unit, a second image generation unit, and a region discrimination unit. The light source unit emits a plurality of types of illumination light beams with different wavelengths. The image sensor images an observation target, using the respective illumination light beams, and the image acquisition unit that acquires images corresponding to the respective illumination light beams. The first image generation unit generates a first image serving as a base of a display image to be displayed on a display unit, using any of the images acquired by the image acquisition unit. The second image generation unit generates a second image, using at least one image having a different corresponding wavelength from the image used for the generation of the first image among the images acquired by the image acquisition unit. The region discrimination unit that discriminates a region in the observation target, using the second image.

It is preferable that the endoscope system further comprises an enhancement processing unit that generates the display image in which at least one region among the regions discriminated by the region discrimination unit is enhanced, using the first image.

It is preferable that the second image generation unit generates the second image, using at least one of the images acquired at different timings from that of the image to be used for the generation of the first image among the images corresponding to the respective illumination light beams.

It is preferable that the image sensor has a plurality of color filters with different colors, and the image acquisition unit acquires the image for each of the illumination light beams and for each of the color filters, in a case where the observation target is imaged using the illumination light beams.

It is preferable that the second image generation unit generates the second image using one or a plurality of the images.

It is preferable that the region discrimination unit discriminates any one or more among a region that is a dark part of the observation target, a halation region, a region with blood vessels, or a region to which a residue or a residual liquid is adhered.

The endoscope system further comprises a region discrimination setting unit that sets the type of the regions to be discriminated by the region discrimination unit; and a light source control unit that controls the type of the illumination light beams to be emitted in accordance with the type of the regions set by the region discrimination setting unit.

It is preferable that the second image generation unit generates a plurality of the mutually different second images, and the region discrimination unit discriminates a different type of region for each of the second images.

It is preferable that, in a case where the region discrimination unit discriminates a plurality of regions, the enhancement processing unit generates the display image by changing an enhancement method for every region discriminated by the region discrimination unit.

It is preferable that the endoscope system further comprises a support information calculation unit that calculates information for supporting diagnosis about the regions discriminated by the region discrimination unit.

A processor device of the invention is a processor device for an endoscope system including a light source unit and an image sensor, and comprises an image acquisition unit, a first image generation unit, a second image generation unit, and a region discrimination unit. The light source unit emits a plurality of types of illumination light beams with different wavelengths. The image sensor images an observation target, using the respective illumination light beams. The image acquisition unit acquires images corresponding to the respective illumination light beams. The first image generation unit generates a first image serving as a base of a display image to be displayed on a display unit, using any of the images acquired by the image acquisition unit. The second image generation unit generates a second image, using at least one image having a different corresponding wavelength from the image used for the generation of the first image among the images acquired by the image acquisition unit. The region discrimination unit that discriminates a region in the observation target, using the second image.

A method of operating an endoscope system of the invention comprises a step of emitting a plurality of types of illumination lights with different wavelengths, by a light source. The method of operating an endoscope system of the invention comprises a step of imaging an observation target, using the respective illumination light beams, by an image sensor. The method of operating an endoscope system of the invention comprises a step of acquiring images corresponding to the respective illumination light beams by an image acquisition unit. The method of operating an endoscope system of the invention comprises a step of generating a first image serving as a base of a display image to be displayed on a display unit, using any of the images acquired by the image acquisition unit, by a first image generation unit. The method of operating an endoscope system of the invention comprises a step of generating a second image, using at least one image having a different corresponding wavelength from that of the image used for the generation of the first image among the images acquired by the image acquisition unit, by a second image generation unit. Additionally, the method of operating an endoscope system of the invention comprises a step of discriminating the regions in the observation target using the second image, by a region discrimination unit.

According to the endoscope system, the processor device, and the method of operating an endoscope system of the invention, a plurality of regions having different features can be substantially simultaneously and accurately discriminated.

DESCRIPTION OF THE PREFERRED EMBODIMENTS

Figure 1:
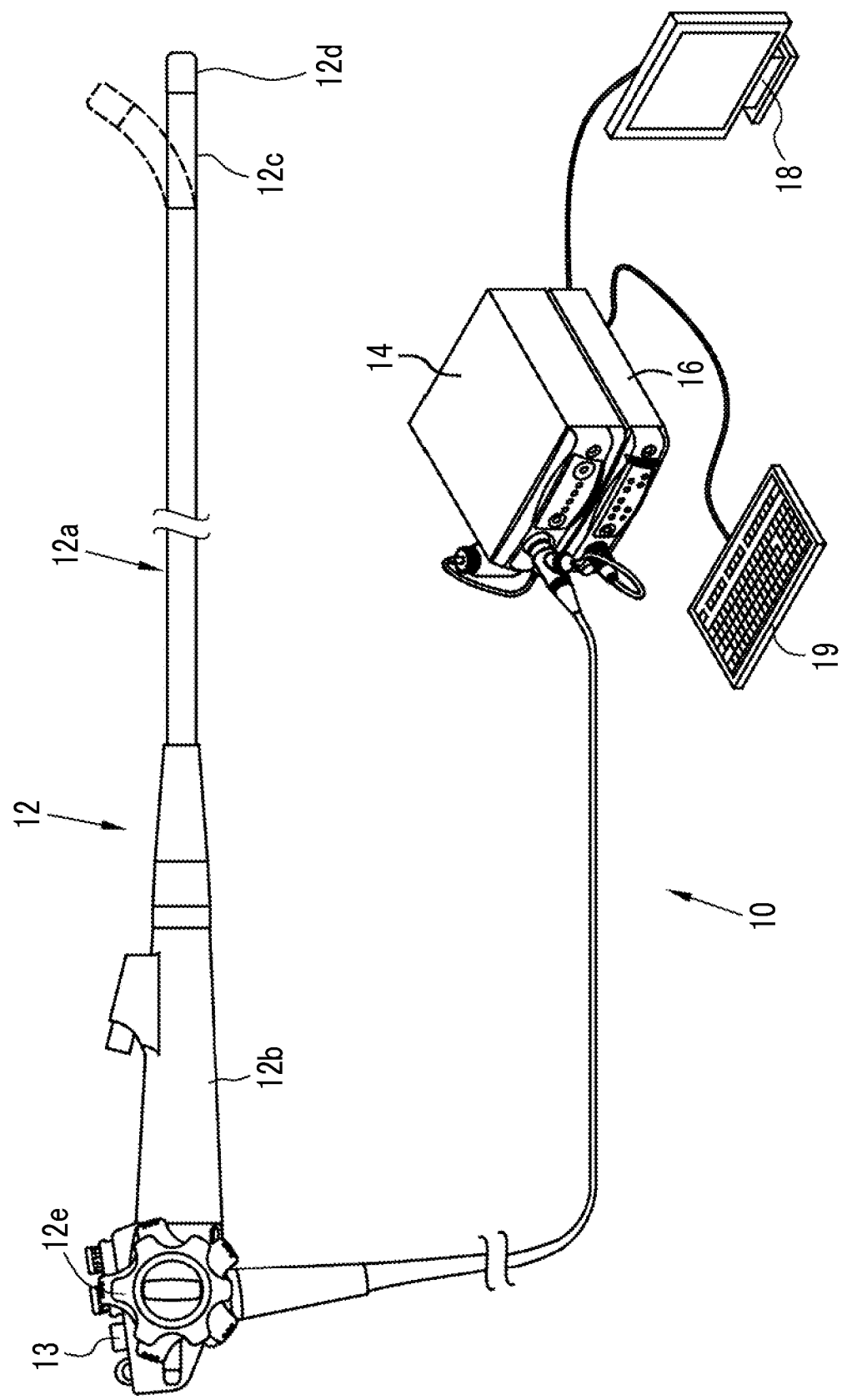
FIG. 1 is an external view of an endoscope system.

As illustrated in FIG. 1, an endoscope system 10 comprises an endoscope 12, a light source device 14, a processor device 16, a monitor 18, and a console 19. The endoscope 12 images an observation target. The light source device 14 generates illumination light. The processor device 16 performs system control, image processing, and the like of the endoscope system 10. The monitor 18 is a display unit that displays a display image (hereinafter, referred to as a display image 121, refer to FIG. 11) generated by the processor device 16. The console 19 is an input device that performs setting input and the like to the processor device 16 and the like.

The endoscope 12 has an insertion part 12a to be inserted into a subject, an operating part 12b provided at a proximal end portion of the insertion part 12a, a bending part 12c provided on a distal end side of the insertion part 12a, and a distal end part 12d. By operating an angle knob 12e of the operating part 12b, the bending part 12c is bent. As the bending part 12c is bent, the distal end part 12d is directed in a desired direction. In addition, the distal end part 12d is provided with a jet port (not illustrated) that jets air, water, or the like toward the observation target. Additionally, the operating part 12b is provided with a zoom operating part 13 in addition to the angle knob 12e. By operating of the zoom operating part 13, the observation target can be enlarged or reduced for imaging.

Figure 2:
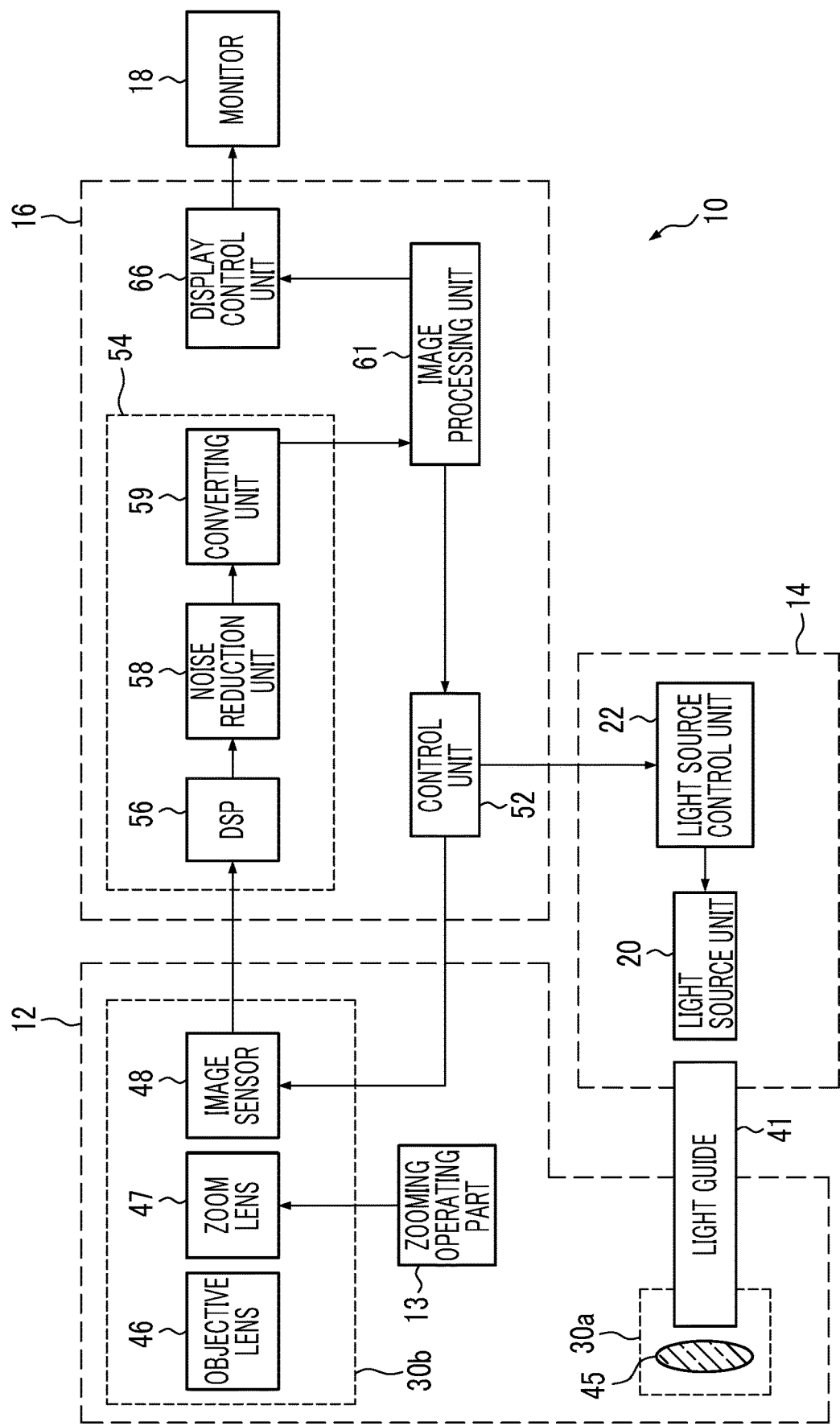
FIG. 2 is a block diagram of the endoscope system.

As illustrated in FIG. 2, the light source device 14 comprises a light source unit 20 that emits the illumination light, and a light source control unit 22 that controls driving of the light source unit 20.

The light source unit 20 comprises, for example, a plurality of light emitting diodes (LEDs) that emit light having different central wavelengths or wavelength ranges (hereinafter, simply referred to as "having different wavelengths") as light sources, and a plurality of type of illumination light beams having different wavelengths can be emitted depending on light emission or turn-on of the respective LEDs, adjustment of light quantity, or the like. For example, the light source unit 20 is capable of emitting broadband purple light, blue light, green light, and red light with relatively wide wavelength ranges as the illumination light beams, respectively. Particularly, the light source unit 20 is capable of emitting narrowband (means that the wavelength range is a range of about 10 nm to 20 nm) purple light, blue light, green light, and red light as the illumination light beams, in addition to the broadband purple light, blue light, green light, and red light. More specifically, the light source unit 20 is capable of emitting narrowband purple light with a central wavelength of about 400 nm, first narrowband blue light with a central wavelength of about 450 nm, second narrowband blue light with a central wavelength of about 470 nm, narrowband green light with a central wavelength of about 540 nm, and narrowband red light with a central wavelength of about 640 nm, as the illumination light beams. In addition, the light source unit 20 is capable of emitting white light as an illumination light beam by combining the broadband or narrowband purple light, blue light, green light, and red light with each other. Additionally, in the present embodiment, there is a case where the light source unit 20 emits narrowband mixed light formed by the first narrowband blue light, the narrowband green light, and the narrowband red light as an illumination light beam.

In addition, instead of the LEDs, a combination of a laser diode (LD), a fluorescent body, and a band limiting filter, a combination of a lamp, such as a xenon lamp, and a band limiting filter, or the like can be used for the light source unit 20. It is natural that, even in a case where the LEDs constitute the light source unit 20, the fluorescent body or the band limiting filter can be used in combination with the LEDs.

The light source control unit 22 independently controls the timing of ON/OFF of the respective light sources that constitute the light source unit 20, the light emission amount thereof at the time of ON, and the like. As a result, the light source unit 20 is capable of emitting the plurality of types of illumination light beams with different wavelengths. Additionally, the light source control unit 22 controls the light source unit 20 in conformity with timing (so-called frame) for imaging of an image sensor 48. In the present embodiment, the light source unit 20 sequentially and repeatedly emits the white light, the narrowband purple light, the second narrowband blue light, and the narrowband mixed light as the illumination light beams, respectively, in conformity with imaging frames of the image sensor 48 by the control of the light source control unit 22.

Additionally, the light source control unit 22 controls the types of the illumination light emitted from the light source unit 20 in accordance with the type, number, and the like of regions for region discrimination. Accordingly, the light source control unit 22 suppresses the number of imaging frames required for the region discrimination to a requisite minimum. Specifically, the endoscope system 10 discriminates at least any one or more of a region (hereinafter, a dark part region 102, refer to FIG. 7) that is a dark part of the observation target, a halated region (hereinafter, referred to as a halation region, not illustrated), a region (hereinafter, referred to as a residual liquid region 104, refer to FIG. 7) to which a residue or the residual liquid has adhered, or a region with blood vessels (hereinafter, referred to as a blood vessel region 103, refer to FIG. 7). As a result, in the endoscope system 10, a region where mucous membranes are photographed, and the above dark part region 102, halation region, residual liquid region 104, or blood vessel region 103 are distinguished from each other. In the present embodiment, all the above respective regions are discriminated from each other. Therefore, in the present embodiment, as for the light source control unit 22, the type of illumination light in which the light source unit 20 emits light one by one is set in white light, narrow-band purple light, the second narrow-band blue light, and narrow-band mixture light.

The illumination light emitted from the light source unit 20 is incident on a light guide 41. The light guide 41 is built within the endoscope 12 and a universal cord, and propagates the illumination light up to the distal end part 12d of the endoscope 12. The universal cord is a cord that connects the endoscope 12, and the light source device 14 and the processor device 16 together. In addition, multi-mode fiber can be used as the light guide 41. As an example, a fine-diameter fiber cable of which the core diameter is 105 µm, the clad diameter is 125 µm, and a diameter including a protective layer serving as an outer cover is φ0.3 to 0.5 mm can be used.

The distal end part 12d of the endoscope 12 is provided with an illumination optical system 30a and an imaging optical system 30b. The illumination optical system 30a has an illumination lens 45, and emits the illumination light toward the observation target via the illumination lens 45. The imaging optical system 30b has an objective lens 46, a zoom lens 47, and an image sensor 48. The image sensor 48 images the observation target, using reflected light or the like (including scattered light, fluorescence emitted from the observation target, fluorescence resulting from medicine administered to the observation target, or the like in addition to the reflected light) of the illumination light returning from the observation target via the objective lens 46 and the zoom lens 47. The zoom lens 47 is moved by operating the zoom operating part 13, and enlarges or reduces the observation target to be imaged using the image sensor 48.

Figure 3:
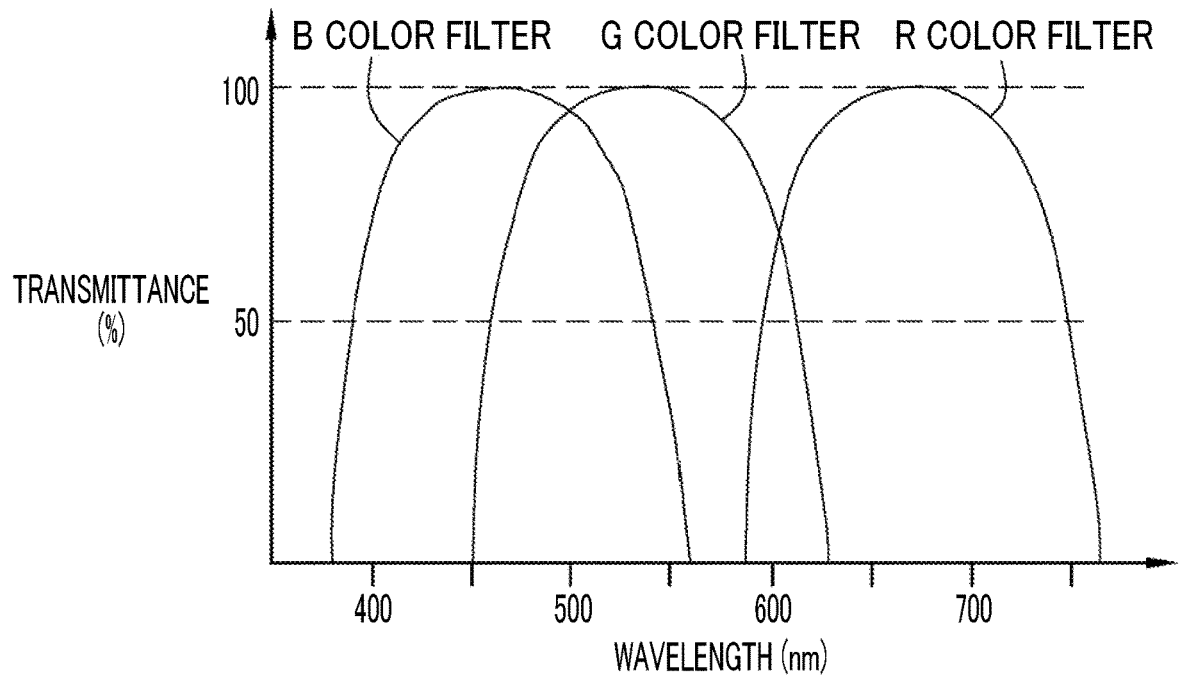
FIG. 3 is a graph illustrating characteristics of color filters.

The image sensor 48 has a plurality of color filters with different colors. The image sensor 48 is, for example, a color sensor having color filters of a primary color system, and comprises three types of pixels of a B pixel (blue pixel) having a blue color filter, a G pixel (green pixel) having a green color filter, and an R pixel (red pixel) having a red color filter. As illustrated in FIG. 3, the blue color filter allows mainly purple to blue light to be transmitted therethrough. The green color filter allows mainly green light to be transmitted through. The red color filter allows mainly red light to be transmitted therethrough. In a case where the observation target of the primary color system is imaged using the image sensor 48 as described above, three types of images including a B image (blue image) obtained from the B pixel, a G image (green image) obtained from the G pixel, and an R image (red image) obtained from the R pixel can be simultaneously obtained to the maximum.

In addition, as the image sensor 48, a charge coupled device (CCD) image sensor or a complementary metal-oxide semiconductor (CMOS) image sensor is available. Additionally, although the image sensor 48 of the present embodiment is the color sensor of the primary color system, a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the above respective color pixels in a case where the color sensor of the complementary color system is used can be converted into the B image, the G image, and the R image in a case where complementary color-primary color conversion is performed. Additionally, instead of the color sensor, a monochrome sensor that is not provided with the color filters can be used as the image sensor 48. In this case, the above respective color images can be obtained by sequentially imaging the observation target, using the respective illumination light beams in colors, such as BGR.

The processor device 16 has a control unit 52, an image acquisition unit 54, an image processing unit 61, and a display control unit 66.

The processing unit 52 performs overall control of the endoscope system 10, such as synchronous control between radiation timing of the illumination light and timing of the imaging. In a case where it additionally sets a type, number, or the like of regions which carry out region discrimination using console 19 or the like, as for the control unit 52, the setting is input to the light source control unit 22.

The image acquisition unit 54 acquires an image of the observation target from the image sensor 48. In the present embodiment, the image sensor 48 has the color filters. Thus, the image acquisition unit 54 acquires an image for each illumination light beam and for each color filter. That is, using one arbitrary illumination light, an image sensor 48 will acquire 1 time of a plurality of images to which the image acquisition unit 54 corresponded to the color of each color filter for an observation target, in a case where it images.

The image acquisition unit 54 has a digital signal processor (DSP) 56, a noise reduction unit 58, and a converting unit 59, and performs various kinds of processing on an acquired image, as needed, using these units.

The DSP 56 performs various kinds of processing, such as defect correction processing, offset processing, gain correction processing, linear matrix processing, gamma conversion processing, demosaicing processing, and YC conversion processing, on the acquired image, as needed.

The defect correction processing is the processing of correcting the pixel value of a pixel corresponding to a defective pixel of the image sensor 48. The offset processing is the processing of reducing a dark current component from the images subjected to the defect correction processing, and setting an accurate zero level. The gain correction processing is the processing of adjusting a signal level of each image by multiplying the images subjected to the offset processing by a gain. The linear matrix processing is the processing of enhancing color reproducibility on the images subjected to the offset processing, and the gamma conversion processing is the processing of adjusting the brightness and saturation of the images after the linear matrix processing. The demoisaicing processing (also referred to as equalization processing or synchronization processing) is the processing of interpolating the pixel value of a missing pixel, and is performed on the images after the gamma conversion processing. The missing pixel is a pixel with no pixel value due to the arrangement of the color filters (because other color pixels are disposed in the image sensor 48). For example, since the B image is an image obtained by imaging the observation target in the B pixel, there is no pixel value in pixels at positions corresponding to the G pixel and the R pixel. In the demosaicing processing, the pixel values of the pixels at the positions of the G pixel and the R pixel of the image sensor 48 are generated by interpolating the B image. The YC conversion processing is the processing of converting the images after the demosaicing processing into a luminance channel Y, a color difference channel Cb, and a color difference channel Cr.

The noise reduction unit 58 performs noise reduction processing using, for example, a moving average method, a median filter method, or the like, on the luminance channel Y, the color difference channel Cb, and the color difference channel Cr. The converting unit 59 re-converts the luminance channel Y, the color difference channel Cb, and the color difference channel Cr after the noise reduction processing into images in respective colors of BGR.

Figure 4:
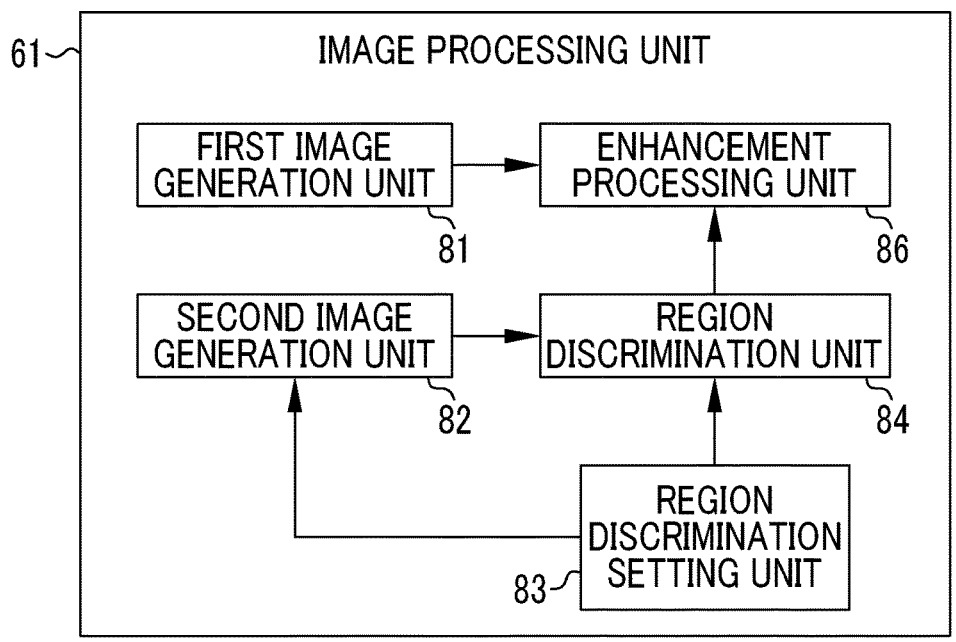
FIG. 4 is a block diagram of an image processing unit.

The image processing unit 61 generates a display image 121 to be displayed on the monitor 18, using the images acquired by the image acquisition unit 54. For this reason, as illustrated in FIG. 4, the image processing unit 61 comprises a first image generation unit 81, a second image generation unit 82, a region discrimination setting unit 83, a region discrimination unit 84, and an enhancement processing unit 86.

A first image generation unit 81 generates a first image, using any of the images acquired by the image acquisition unit 54. The first image is an image serving as a base of the display image 121 to be displayed on the monitor 18 that is the display unit. In the present embodiment, the first image a natural-color white light image 101 (refer to FIG. 7) obtained by imaging the observation target, using the white light for the illumination light. In addition, in a case where the first image is generated, the first image generation unit 81 performs color conversion processing, color enhancement processing, and structure enhancement processing on the images acquired by the image acquisition unit 54, as needed. In the color conversion processing, 3×3 matrix processing, gradation transformation processing, three-dimensional look-up table (LUT) processing, and the like are performed on the images in the respective colors of BGR. The color enhancement processing is the processing of enhancing the colors of an image, and the structure enhancement processing is the processing of enhancing, for example, the tissue or structure of the observation target, such as blood vessels or pit patterns.

The second image generation unit 82 generates the second image that is different from the first image among the images which the image acquisition unit 54 acquired using 1 or a plurality of images. More specifically, the second image generation unit 82 generates the second, using at least one image with a different wavelength, corresponding to the image used for the generation of the first image, among the images acquired by the image acquisition unit 54, The second image is a region discrimination image to be used for the region discrimination performed by the region discrimination unit 84. The "different from the first image" basically means that the image to be used for the generation of the second image by the second image generation unit 82 is different from the image to be used for the generation of the first image by the first image generation unit 81 in terms of type, number, or combination. That is, the second image is an image substantially different from the first image in terms of the distinguishability of the tissue, structure, or the like of the observation target in a case where the type, number, or combination of images to be used differs. For example, when the first image generation unit 81 generates the first image using three kinds of images, the image generated using one or a plurality of images different from the three types of images is the second image. An image obtained by performing processing, such as the structure enhancement processing, on one type of image selected from the three types of images to be used for the generation of the first image or one type of image selected from the images to be used for the first image is also the second image. An image generated by performing operation or the like using two types of images of the three types of images to be used for the generation of the first image, an image generated by performing operation or the like after a separate image is further added to the three types of images to be used for the generation of the first image, or the like is also the second image.

In the present specification, the "second image different from the first image" also includes an image generated by performing operation using the images to be used for the generation of the first image, an image obtained by changing the importance of various kinds of processing for the images to be used for the generation of the first image, or the like, even in a case where the first image generation unit 81 uses the same images as the images to be used for the generation of the first image in terms of type, number, and combination. This is because these images are also structure different from the first image in terms of the distinguishability of the tissue, structure, or the like of the observation target.

The second image generation unit 82 generates one or a plurality of the second images on the basis of settings for the region discrimination. The settings for the region discrimination are, specifically, the types or the like of regions to be discriminated, and the region discrimination setting unit 83 performs the settings for the region discrimination on the basis of input using the input device, such as the console 19.

The region discrimination setting unit 83 sets the type, light quantity, and light-emitting order, and the like of the illumination light in accordance with the types of regions to be discriminated in a case where the types of regions to be discriminated are set. Hereinafter, the settings for the region discrimination includes the type, light quantity, light-emitting order, and the like of the illumination light to be secondarily set in accordance with the types of regions to be discriminated, in addition to the types of regions to be discriminated. The region discrimination setting unit 83 is capable of respectively and individually setting whether or not the region discrimination is performed on the dark part region 102, the halation region, the blood vessel region 103, or the residual liquid region 104. Hence, the second image generation unit 82 selectively generates the second image to be used for the region discrimination on the basis of the settings for the region discrimination.

In the present embodiment, the settings for the region discrimination are settings in which all the dark part region 102, the halation region, the residual liquid region 104, and the blood vessel region 103 are discriminated from each other. For this reason, the second image generation unit 82 generates an image (hereinafter referred to as a bright/dark region discrimination image 112, refer to FIG. 8) for discriminating the dark part region 102 and the halation region from each other, an image (hereinafter, referred to as a blood vessel region discrimination image 113, refer to FIG. 9) for discriminating the blood vessel region 103, and an image (hereinafter referred to as a residual liquid region discrimination image 114, refer to FIG. 10) for discriminating the residual liquid region 104.

The bright/dark region discrimination image 112 is an image in which the brightness and dankness of the observation target is clear as compared to the first image. The second image generation unit 82 generates the bright/dark region discrimination image 112, for example, by operating the images to be used for the generation of the first image. In this case, the bright/dark region discrimination image 112 is generally an image in which the distribution of the luminance of the first image is enhanced.

The residual liquid region discrimination image 114 is an image in which the presence or absence, the profile, and the like of the residue and the residual liquid are made clear as compared to the first image. The second image generation unit 82 generates the residual liquid region discrimination image 114, for example, by using at least one image that is different from the images to be used for the generation of the first image and is acquired at a timing different from that of the images to be used for the generation of the first image.

The blood vessel region discrimination image 113 is an image in which the presence or absence, profile, and the like of specific blood vessels (blood vessels present in an extreme surface layer of the mucous membrane in the present embodiment) are made clear as compared to the first image. The second image generation unit 82 generates the blood vessel region discrimination image 113, for example, by using an image that is different from the images to be used for the generation of the first image and is acquired from a timing different from that of the images to be used for the generation of the first image.

All the bright/dark region discrimination image 112, the blood vessel region discrimination image 113, and the residual liquid region discrimination image 114 are the second images, and are respectively different from the first image in terms of the type, number, or combination of the images to be used for the generation or the operation, the importance of processing, or the like during generation. Additionally, the bright/dark region discrimination image 112, the blood vessel region discrimination image 113, and the residual liquid region discrimination image 114 are different from each other in terms of the type, number, or combination of the images to be used for the generation or the operation, the importance of processing, or the like during generation. For this reason, the second image generation unit 82 generates a plurality of mutually different second images including the bright/dark region discrimination image 112, the blood vessel region discrimination image 113, and the residual liquid region discrimination image 114.

In addition, the region discrimination setting unit 83 also inputs the settings for the region discrimination to the control unit 52. Then, control unit 52 inputs the settings for the region discrimination to the light source control unit 22. As a result, the light source control unit 22 controls the type, light quantity, light-emitting order, and the like of the illumination light emitted from the light source unit 20 in accordance with the types of the regions set by the region discrimination setting unit 83.

The region discrimination unit 84 discriminates regions having specific features in the observation target, using the second image. The discrimination of the respective regions is performed, for example, by utilization of the shapes of a histogram showing the appearance frequency of pixel values, the comparison between preset threshold values and the pixel values, or the like. More specifically, the region discrimination unit 84 discriminates any one or more of the dark part region 102, the halation region, the blood vessel region 103, or the residual liquid region 104 on the basis of the settings for the region discrimination. In a case where the dark part region 102 or the halation region is discriminated, the region discrimination unit 84 uses bright/dark region discrimination image 112 having dark parts and halation clearer than the first image. In a case where the blood vessel region 103 is discriminated, the region discrimination unit 84 uses blood vessel region discrimination image 113 having blood vessels clearer than the first image. Similarly, in a case where the residual liquid region 104 is discriminated, the region discrimination unit 84 uses the residual liquid region discrimination image 114 having the residue and the residual liquid clearer than the first image. That is, in a case where the region discrimination unit 84 discriminates a plurality of regions having different features, the second image generation unit 82 generates a plurality of mutually different second images, and the region discrimination unit 84 discriminates different types of regions for each of the second images.

The enhancement processing unit 86 generates the display image 121 in which at least one region of the regions discriminated by the region discrimination unit 84 is enhanced, using the first image. Particularly, in the present embodiment, the enhancement processing unit 86 generates the display image 121 by changing an enhancement method for each of the regions discriminated by the region discrimination unit 84. The "changing an enhancement method" means changing the type of processing to be performed for each discriminated region or changing the importance of the processing for each discriminated region in a case where tissue or structure present within the regions discriminated by performing frequency enhancement processing, edge enhancement processing, coloration processing, or the like, or the whole discriminated region is improved in distinguishability compared to other regions, such as the mucous membrane.

The display control unit 66 acquires the display image 121 from the image processing unit 61, and converts the acquired display image 121 in a format suitable for display to sequentially output and display the converted display image 121 on the monitor 18. Accordingly, a doctor or the like can observe the observation target, the display image 121.

Figure 5:
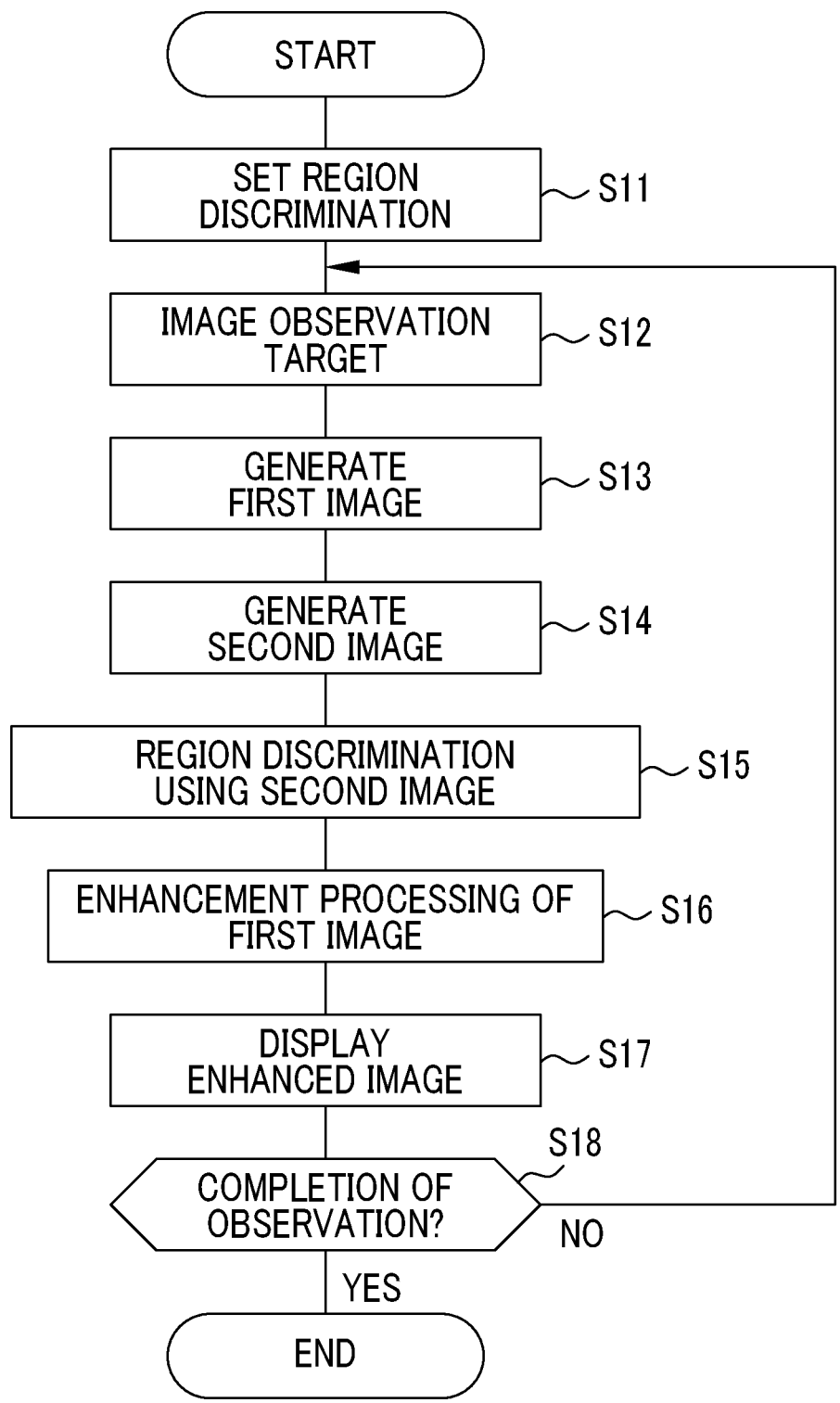
FIG. 5 is a flowchart illustrating the operation of the endoscope system.

Next, a flow of the operation of the endoscope system 10 will be described along a flowchart illustrated in FIG. 5. In a case where the endoscope system 10 is used, first, the settings for the region discrimination are performed using the console 19 or the like (S11). In the present embodiment, all the dark part region 102, the halation region, the blood vessel region 103, and the residual liquid region 104 are effectively set, and the type, light quantity, light-emitting order, and the like of the illumination light for discriminating these respective regions are set.

Figures 6, 7:
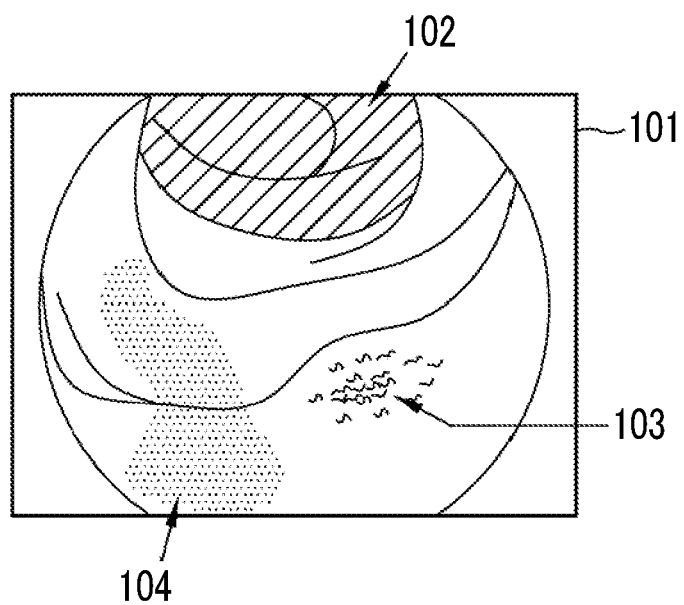
FIG. 6 is an explanatory view illustrating a correspondence relationship between illumination light beams and images to be acquired.
FIG. 7 illustrates a white light image (first image).

As a result, in a case where the observation target is imaged using the endoscope 12 (S12), as illustrated in FIG. 6, in a first frame, the image acquisition unit 54 acquires an image (hereinafter, referred to as a B1 image obtained from the B pixel using the white light for the illumination light, an image (hereinafter, referred to as a G1 image) obtained from the G pixel using the white light from the illumination light, and an image (hereinafter, referred to as an R1 image) obtained from the R pixel using the white light from the illumination light. Next, in a second frame, the image acquisition unit 54 acquires an image (hereinafter, referred to as a B2 image) obtained from the B pixel using the narrowband purple light for the illumination light, an image (hereinafter, referred to as a G2 image) obtained from the G pixel using the narrowband purple light for the illumination light, and an image (hereinafter, referred to as an R2 image) obtained from the R pixel using the narrowband purple light for the illumination light. Next, in the next third frame, the image acquisition unit 54 acquires an image (hereinafter, referred to as a B3 image) obtained from the B pixel using the second narrowband blue light for the illumination light, an image (hereinafter, referred to as a G3 image) obtained from the G pixel using the second narrowband blue light for the illumination light, and an image (hereinafter, referred to as an R3 image) obtained from the R pixel using the second narrowband blue light for the illumination light. Thereafter, in a fourth frame, the image acquisition unit 54 acquires an image (hereinafter, referred to as a B4 image) obtained from the B pixel using the narrowband mixed light for the illumination light, an image (hereinafter, referred to as a G4 image) obtained from the G pixel using the narrowband mixed light for the illumination light, and an image (hereinafter, referred to as an R4 image) obtained from the R pixel using the narrowband mixed light for the illumination light.

As described above, in a case where the observation target is imaged and the various images are acquired, the first image generation unit 81 generates the white light image 101 that is the first image, using the B1 image, the G1 image, and the R1 image, which are obtained in the first frame (S13). As illustrated in FIG. 7, since the white light image 101 is mostly easily observed in that a doctor or the like that displays the observation target in natural color is most familiar with the white light image 101, the white light image 101 is an optimal image for the base of the display image 121. However, it is difficult to observe the observation target because the back of the lumen where the illumination light is difficult to reach becomes the dark part region 102. Additionally, a boundary between a dark part and a bright part is also obscure, and it is difficult to discriminate the dark part region 102 at least in the boundary. Additionally, in the white light image 101, there is also a case where the blood vessel region 103 in which the blood vessels present in the extreme surface layer of the mucous membrane are present can be discriminated. However, it is basically difficult to observe the blood vessels of the blood vessel region 103. Moreover, in the white light image 101, there is also a case where the residual liquid region 104 can be discriminated depending on the concentration of the residual liquid or the like, the breadth of a residual range, or the like. However, there is also a case where it is difficult to discriminate the residual liquid region 104 depending on the concentration of the residual liquid or the like, the breadth of a residual range, or the like. In addition, in the white light image 101, there is a case where there is a region that causes a variation due to specular reflection or the like of the illumination light from the surface of the mucous membrane. However, since a region where the mucous membrane or the like can be normally can be observed is essentially the same as the dark part region 102 in that the brightness thereof has an extreme value, illustration or the like of a halation region is omitted.

The endoscope system 10 generates the white light image 101 (first image) in the first image generation unit 81 as described above, and generates second images in order to discriminate the respective regions in the second image generation unit 82 (S14). Specifically, the second image generation unit 82 generates three types of second images of the bright/dark region discrimination image 112, the blood vessel region discrimination image 113, and the residual liquid region discrimination image 114. Then, the region discrimination unit 84 performs the region discrimination, using these second images (S15). Specifically, the region discrimination unit 84 discriminates the dark part region 102, using the bright/dark region discrimination image 112 (also including the discrimination of the halation region in a case where the dark part region 102 is present) Additionally, the region discrimination unit 84 discriminates the blood vessel region 103, using the blood vessel region discrimination image 113, and discriminates the residual liquid region 104, using the residual liquid region discrimination image 114.

Figure 8:
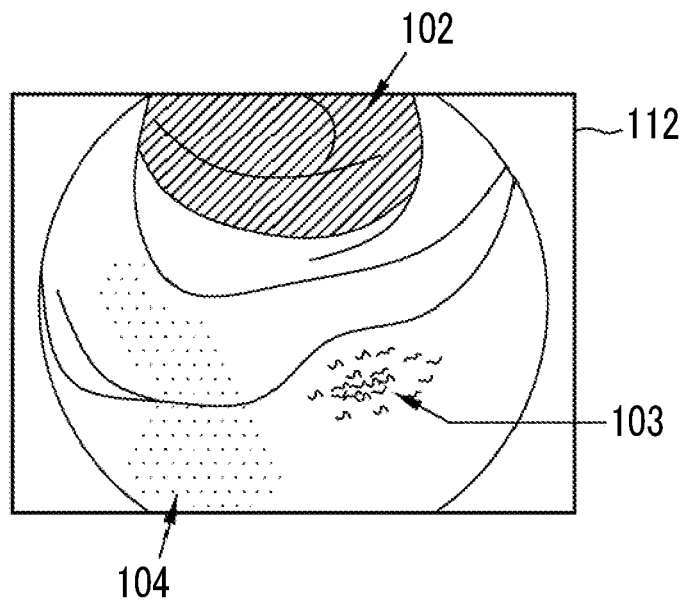
FIG. 8 illustrates a bright/dark region discrimination image (second image).

The second image generation unit 82 operates the luminance of the observation target, using the B1 image, the G1 image, and the R1 image, which are acquired in the first frame, and generates the bright/dark region discrimination image 112 showing the distribution of the luminance. For this reason, as illustrated in FIG. 8, the boundary between the dark part region 102 and a bright part region in the bright/dark region discrimination image 112 becomes clear compared to the white light image 101. Meanwhile, in the bright/dark region discrimination image 112, the distinguishability of the blood vessel region 103 and the residual liquid region 104 is equal to or less than that of the white light image 101. Hence, the region discrimination unit 84 can discriminate the dark part region 102 more accurately than in a case where the white light image 101 is used by using the bright/dark region discrimination image 112. The same applies to a case where there is the halation region.

Figure 9:
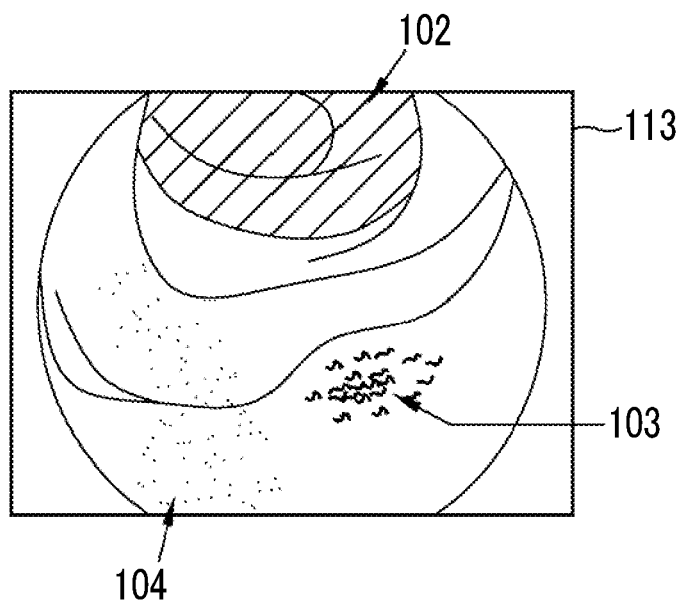
FIG. 9 illustrates a blood vessel region discrimination image (second image).

Additionally, the second image generation unit 82 generates the blood vessel region discrimination image 113, using the B2 image acquired in the second frame and the B4 image acquired in the fourth frame. More specifically, the second image generation unit 82 first calculates a differential image between the B2 image and the B4 image (for example, an image obtained by subtracting the B4 image from the B2 image or a ratio image (for example, B2 image/B4 image). Then, the blood vessel region discrimination image 113 is generated by allocating one of the B2 image or the B4 image to a luminance channel and allocating the above differential image or ratio image to a color difference channel. In the blood vessel region discrimination image 113 generated in this way, as illustrated in FIG. 9, the blood vessels present in the blood vessel region 103 is clearer than the white light image 101 by virtue of a difference in color from the mucous membrane due to a difference in depth of invasion of the first narrowband blue light included in the narrowband purple light and the narrowband mixed light into a portion under the mucous membrane. Meanwhile, in the blood vessel region discrimination image 113, the distinguishability of the dark part region 102 and the residual liquid region 104 decreases relatively compared to the blood vessels of the blood vessel region 103, and the distinguishability of these regions is equal to or less than that of the white light image 101. For this, by using the blood vessel region discrimination image 113, the region discrimination unit 84 can discriminate the blood vessel region 103 more accurately than in a case where the white light image 101 is used.

Additionally, the second image generation unit 82 generates the residual liquid region discrimination image 114, using the B3 image acquired in the third frame, and the B4 image, the G4 image, and the R4 image, which are acquired in the fourth frame, More specifically, the second image generation unit 82 first calculates a ratio of the B4 image to the G4 image (hereinafter, referred to as B4/G4), a ratio of the B3 image to the G4 image (hereinafter, referred to as B3/G4, and a ratio of the R4 image to the G4 image (hereinafter, referred to as R4/G4). Next, an operation value "Z" is calculated according to Equation 1. A phase $\phi$ in the Equation 1 is determined such that the operation value "Z" is invariable with respect to the oxygen saturation of hemoglobin contained in the observation target. The phase $\phi$ can be obtained in advance by experiment or the like.

$$Z=(B4/G4)\times\cos\phi-(B3/G4)\times\sin\phi \quad \text{[Equation 1]}$$

The operation value "Z" is a certain value according to the ratio R4/G4 irrespective of the oxygen saturation of the observation target in a case where there is no residual liquid containing yellow coloring agent, such as bilirubin. Meanwhile, the operation value "Z" does not depend on the oxygen saturation of the observation target in a case where there is a residual liquid or the like containing a yellow coloring agent, but varies in accordance with the amount (concentration) of the yellow coloring agent contained in the residual liquid or the like. For this reason, the second image generation unit 82 calculates a variation amount $\Delta$ (=$Z$-$Z_0$) of the operation value "Z" calculated in practice in the value of the ratio R4/G4 calculated in practice, using a value $Z_0$ taken by the operation value "Z" as a reference in a case where there is no residual liquid or the like in the value of the ratio R4/G4 calculated in practice. This variation amount $\Delta Z$ becomes a value showing the presence or absence and amount of the residual liquid. Hence, the second image generation unit 82 generates the residual liquid region discrimination image 114 having the value of the variation amount $\Delta Z$ as a pixel value.

Figure 10:
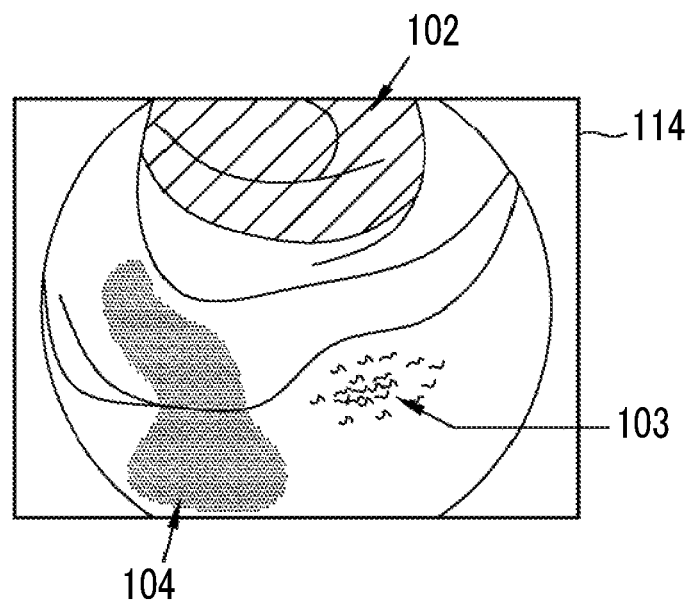
FIG. 10 illustrates a residual liquid region discrimination image (second image).

The residual liquid region discrimination image 114 generated in this way is clear in the presence or absence of the residual liquid region 104 and the difference between the residual liquid region 104 and other regions, such as the mucous membrane, as compared to the white light image 101, as illustrated in FIG. 10. Meanwhile, in the residual liquid region discrimination image 114, the distinguishability of the dark part region 102 and the blood vessel region 103 is equal to or less than the white light image 101. Hence, by using the residual liquid region discrimination image 114, the region discrimination unit 84 can discriminate the residual liquid region 104 more accurately than in a case where the white light image 101 or the like is used.

In addition, usually, in a case where the presence or absence and amount of the residual liquid or the like are used, it is easy to utilize the absorption quantity of the blue light resulting from the yellow coloring agent contained in the residual liquid or the like. However, the blue light varies due to the oxygen saturation of the hemoglobin contained in the observation target. As a result, there is a case where an inaccurate result may be brought in a case where the presence or absence and amount of the residual liquid or the like, are measured simply on the basis of the absorption quantity (for example, the pixel value of the B1 image to be used for the generation of the white light image 101) of blue light. Hence, in the present embodiment, using the B4 image that varies largely in value due to the presence or absence and amount of the yellow coloring agent and does not varies substantially in value due to the value of the oxygen saturation, and the B3 image that varies in value to the same extent as that of the B4 image due to the presence or absence and amount of the yellow coloring agent and varies largely in value due to the value of the oxygen saturation, the dependability of the oxygen saturation is substantially eliminated, and the operation value "Z" that varies substantially in value due to the presence or absence and amount of the yellow coloring agent is utilized.

In a case where the region discrimination unit 84 discriminates the dark part region 102, the halation region, the blood vessel region 103, and the residual liquid region 104, the enhancement processing unit 86 generates the display image 121 by performing the enhancement processing on the respective regions determined by the region discrimination unit 84 in the white light image 101 that is the first image (S16). Then, the display control unit 66 displays the display image 121 output from the enhancement processing unit 86 on the monitor 18 (S17). The endoscope system 10 repeatedly performs the above operation until the completion of the observation or changes in the settings for the region discrimination (S18).

As described above, in a case where the endoscope system 10 performs the region discrimination, the second image suitable for the region discrimination is generated separately from the first image suitable for the display. Then, the region discrimination is performed not using the first image but using the second image. For this reason, as in the related-art endoscope system, as compared to a case where the region discrimination is performed using an image (the first image in the endoscope system 10) suitable for the display, the endoscope system 10 has high accuracy in the region discrimination. Particularly, in a case where a plurality of regions are discriminated, a difference in the accuracy of the region discrimination is remarkable between the related-art endoscope system and the endoscope system 10. Additionally, the endoscope system 10 can discriminate the plurality of regions substantially simultaneously.

Figure 11:
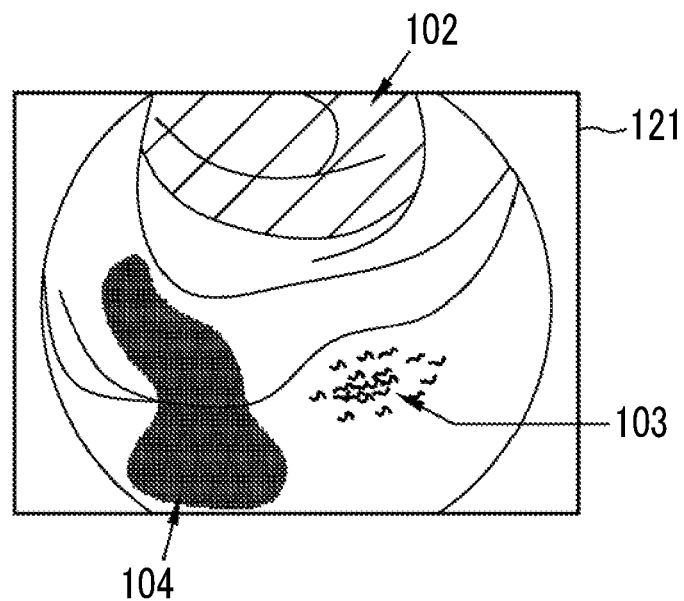
FIG. 11 illustrates a display image.

Moreover, the endoscope system 10 enhances the regions discriminated by the region discrimination unit 84 in the white light image 101 (first image) suitable for the display, instead of displaying the second image to be used for the region discrimination. For this reason, in the display image 121 of the endoscope system 10, as illustrated in FIG. 11, similarly to the white light image 101, the observation target can basically be naturally observed, and tissue, structure, or the like can be accurately enhanced in the respective discriminated regions.

Figure 12:
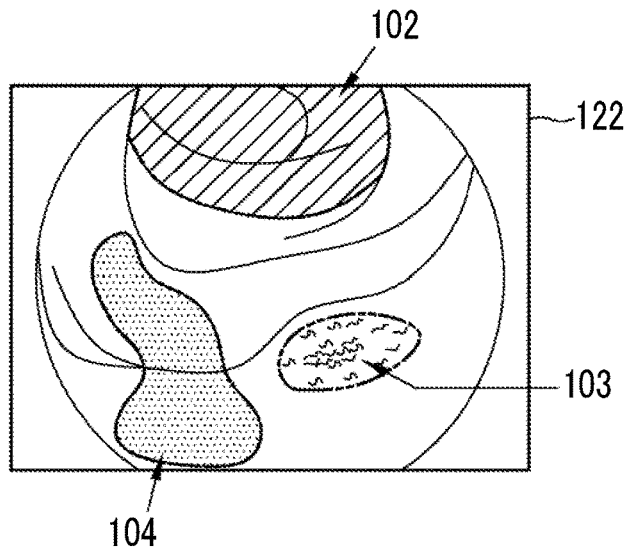
FIG. 12 illustrates another display image.

In addition, in the above embodiment, the display image 121 improves the visibility of the observation target in the dark part region 102, improves the visibility of the blood vessels present in the blood vessel region 103 in the blood vessel region 103, and improves the visibility of the residual liquid or the like in the residual liquid region 104. However, the presence of the respective regions may instead be enhanced by displaying the profiles of the respective regions discriminated by the region discrimination unit 84 as in the display image 122 illustrated in FIG. 12. In this case, it is preferable that the profiles of the respective regions discriminated by the region discrimination unit 84 indicate what kind of region is present by color, line type, coloring within the regions, or the like.

Figure 13:
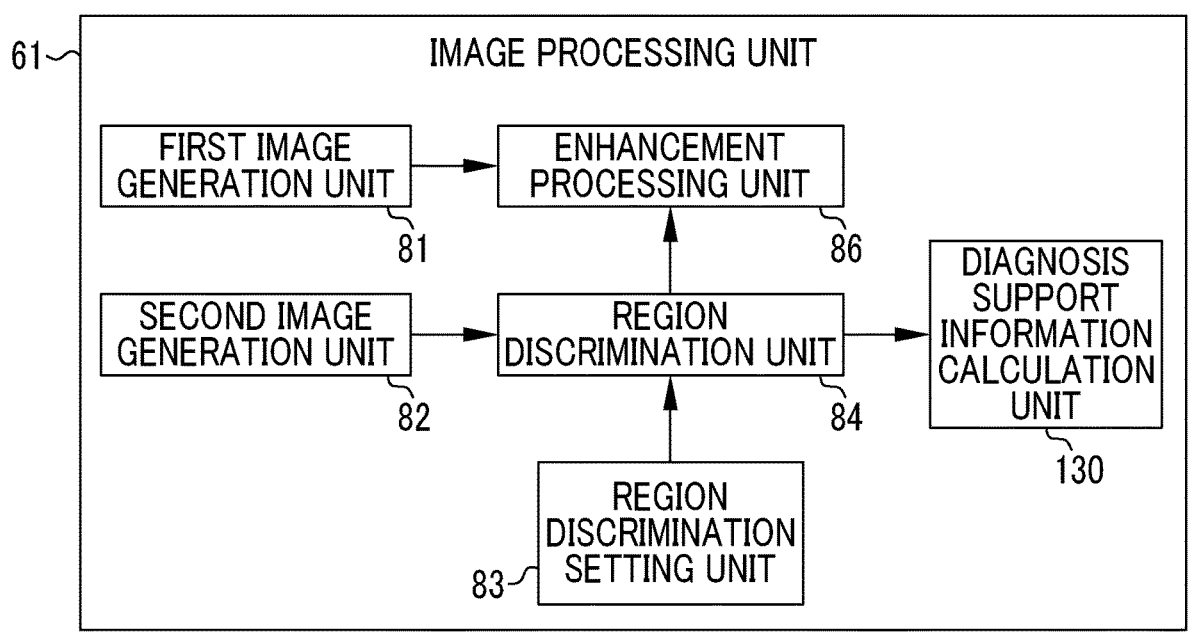
FIG. 13 is a block diagram of the image processing unit provided with a diagnosis support information calculation unit.

In the above embodiment, the display image 121 that has enhanced the regions discriminated by the region discrimination unit 84 is displayed on the monitor 18. However, instead of generating and displaying the display image 121 or after generating and displaying the display image 121, information for supporting diagnosis may be calculated about the regions discriminated by the region discrimination unit 84. In this case, as illustrated in FIG. 13, the image processing unit 61 is provided with a diagnosis support information calculation unit 130. The diagnosis support information calculation unit 130 calculates the information (hereinafter referred to as diagnosis support information) for supporting diagnosis about the regions discriminated by the region discrimination unit 84. The diagnosis support information is, for example, an index indicating the possibility of being a lesion, or an index (for example, the oxygen saturation or the like) capable of determining the possibility that the region is a lesion.

Since the diagnosis support information calculation unit 130 obtains the diagnosis support information about the regions discriminated by the region discrimination unit 84, it is not necessary to calculate the diagnosis support information about the entire image to display. Additionally, the diagnosis support information calculation unit 130 calculates the diagnosis support information only within a required region among the regions discriminated by the region discrimination unit 84, such as calculating the diagnosis support information only about the blood vessel region 103. Usually, the calculation of the diagnosis support information is heavy processing that requires much time or machine power However, as described above, the diagnosis support information calculation unit 130 calculates the diagnosis support information only within the required region that is accurately discriminated. Thus, the diagnosis support information can be accurately calculated with a lightweight operation amount that can be realized. This is particularly useful in a case where the diagnosis support information is provided in real time.

The information about the regions discriminated by the region discrimination unit 84 can be optionally utilized also in extraction or the like of a three-dimensional structure, in addition to calculating the diagnosis support information as described above.

In the above embodiment, the blood vessel region discrimination image 113 is generated using the images obtained by the two frames pf the second frame and the fourth frame. However, there is a case where the blood vessel region discrimination image 113 can be generated using an image equivalent to one frame, in a case where the blood vessel region discrimination image 113 with improved distinguishability of the blood vessel region 103 is generated by a method different from the above embodiment.

Additionally, as shown in the above embodiment, the second image generation unit 82 can generate the second image, using the image acquired in a plurality of frames. In this way, in a case where the images required for the generation of the second image are generated over the plurality of frames, it is preferable to use the images for the generation of the second image after correction processing, such as alignment processing or blurring correction processing, is performed on the images to be used for the generation of the second image. In a case where the correction processing is performed, region discrimination accuracy is further improved.

In the above embodiment, the number of image sensors 48 is one. However, an image sensor with higher sensitivity (hereinafter referred to as a high-sensitivity sensor) than the image sensor 48 can be jointly used for the endoscope system 10. In a case where the high-sensitivity sensor is jointed used, the observation target is imaged, for example, using the fluorescence emitted from a fluorescent material contained in the observation target or a fluorescent material injected into the observation target, and the obtained fluorescence image can be used for the generation of the second image.

In the above embodiment, the region discrimination unit 84 discriminates any region of the dark part region 102, the halation region, the blood vessel region 103, or the residual liquid region 104. However, these are exemplary. The region discrimination unit 84 is capable of discriminating regions other features in addition to these. For example, a reddened region that is reddened, an atrophied region where the mucous membrane is atrophied, or the like can be discriminated in addition the above respective region or instead of the above respective regions. Additionally, a method in which the region discrimination unit 84 discriminates the dark part region 102, the halation region, the blood vessel region 103, or the residual liquid region 104, respectively, is also an example, and these regions can be discriminated by methods different from the above embodiment. In this case, the method of generating the second image is also changed in accordance with the method of discriminating the regions in the region discrimination unit 84.

Figure 14:
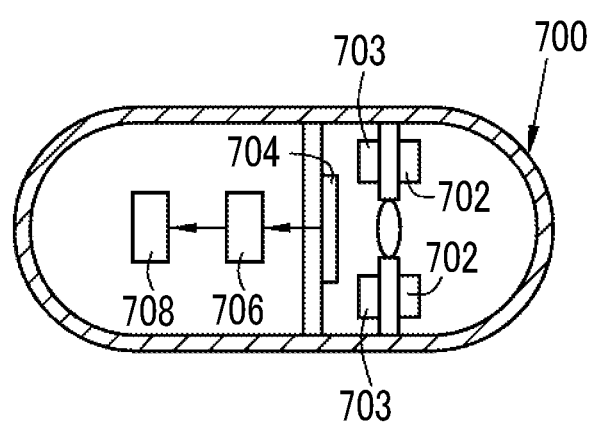
FIG. 14 is a schematic view of a capsule endoscope.

In the above embodiment, the invention is carried out in the endoscope system 10 that performs observation by inserting the endoscope 12 provided with the image sensor 48 into the subject. However, the invention is also suitable in a capsule endoscope system. As illustrated in FIG. 14, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 functions similarly to the light source control unit 22 and the control unit 52. Additionally, the control unit 703 is capable of wirelessly communicating with the processor device of the capsule endoscope system using the transmission/reception antenna 708. Although the processor device of the capsule endoscope system is substantially the same as that of the processor device 16 of the above embodiment, an image processing unit 706 corresponding to the image acquisition unit 54 and the image processing unit 61 is provided in the capsule endoscope 700, and the display image 121 is transmitted to the processor device via a transmission/reception antenna 708. The image sensor 704 is configured similarly to the image sensor 48. EXPLANATION OF REFERENCES 10: endoscope system
12: endoscope
12a: insertion part
12b: operating part
12c: bending part
12d: distal end part
12e: angle knob
13: zoom operating part
14: light source device
16: processor device
18: monitor
19: console
20, 702: light source unit
22: light source control unit
30a: illumination optical system
30b: imaging optical system
41: light guide
45: illumination lens
46: objective lens
47: zoom lens
48, 704: image sensor
52, 703: control unit
54: image acquisition unit
56: DSP
58: noise reduction unit
59: conversion unit
61, 706: image processing unit
66: display control unit
81: first image generation unit
82: second image generation unit
83: region discrimination setting unit
84: region discrimination unit
86: enhancement processing unit
101: white light image
102: dark part region
103: blood vessel region
104: residual liquid region
112: bright/dark region discrimination image
113: blood vessel region discrimination image
114: residual liquid region discrimination image
121, 122: display image
130: diagnosis support information calculation unit
700: capsule endoscope
708: transmission/reception antenna

What is claimed is:

1. An endoscope system comprising:
a light source unit that emits a plurality of types of illumination light beams with different wavelengths;
an image sensor that has a plurality of color filters with different colors and images an observation target, using the respective illumination light beams; and
a processor configured to:
acquire images for each of the illumination light beams and for each of the color filters, upon imaging the observation target by use of the illumination light beams;
generate a first image serving as a base of a display image to be displayed on a display unit, using any of the images acquired;
generates a generate a plurality of second images, using at least one image having a different corresponding wavelength from the image used for the generation of the first image among the images acquired, the processor generating the plurality of second images that are different from each other based on the images acquired for each of the illumination light beams and for each of the color filters;
discriminate a region in the observation target, using the plurality of second images, the processor discriminating a different type of region for each of the second images; and
generate the display image in which at least one region among the regions discriminated is enhanced, using the first image,
wherein in a case where the processor discriminates a plurality of regions, the processor generates the display image by changing an enhancement method for every region discriminated, by changing a type of processing to be performed for each discriminated region or changing an importance of the processing for each discriminated region.

2. The endoscope system according to claim 1,
wherein the processor is further configured to generate the display image in which the presence of the respective regions discriminated are enhanced by displaying profiles of the respective regions.

3. The endoscope system according to claim 1,
wherein the processor is further configured to generate the plurality of second images, using at least one of the images acquired at different timings from that of the image to be used for the generation of the first image among the images corresponding to the respective illumination light beams.

4. The endoscope system according to claim 1,
wherein the processor is further configured to acquire the image for each of the illumination light beams and for each of the color filters, in a case where the observation target is imaged using the illumination light beams.

5. The endoscope system according to claim 1,
wherein the processor is further configured to generate the plurality of second images using one or a plurality of the images.

6. The endoscope system according to claim 1,
wherein the processor is further configured to discriminate any one or more among a region that is a dark part of the observation target, a halation region, a region with blood vessels, or a region to which a residue or a residual liquid is adhered.

7. The endoscope system according to claim 1, wherein the processor is further configured to:
set the type of the regions to be discriminated; and
control the type of the illumination light beams to be emitted in accordance with the type of the regions set by the region discrimination setting unit.

8. The endoscope system according to claim 1,
wherein the processor is further configured to:
generate a plurality of mutually different second images, and
discriminate a different type of region for each of the second images.

9. The endoscope system according to claim 1, wherein the processor is further configured to:
calculate information for supporting diagnosis about the regions discriminated.

10. The endoscope system according to claim 9,
wherein the information for supporting diagnosis is an index indicating a possibility that the region is a lesion, or an index capable of determining a possibility that the region is a lesion.

11. The endoscope system according to claim 10,
wherein the index is an oxygen saturation.

12. A processor device for an endoscope system including a light source unit that emits a plurality of types of illumination light beams with different wavelengths, and an image sensor that has a plurality of color filters with different colors and images an observation target, using the respective illumination light beams, the processing device comprising:
a processor configured to:
acquire images for each of the illumination light beams and for each of the color filters, upon imaging the observation target by use of the illumination light beams;
generate a first image serving as a base of a display image to be displayed on a display unit, using any of the images acquired;
generate a plurality of second images, using at least one image having a different corresponding wavelength from the image used for the generation of the first image among the images acquired, the processor generating the plurality of second images that are different form each other based on the images acquired for each of the illumination light beams and for each of the color filters;
discriminate the regions in the observation target, using the plurality of second images, the processor discriminating a different type of region for each of the second images; and
generate the display image in which at least one region among the regions discriminated is enhanced, using the first image,
wherein in a case where the processor discriminates a plurality of regions, the processor generates the display image by changing an enhancement method for every region discriminated, by changing a type of processing to be performed for each discriminated region or changing an importance of the processing for each discriminated region.

13. A method of operating an endoscope system, comprising:
a step of emitting a plurality of types of illumination lights with different wavelengths, by a light source unit;
a step of imaging an observation target, using the respective illumination light beams, by an image sensor having a plurality of color filters with different colors;
a step of acquiring images for each of the illumination light beams and for each of the color filters, upon imaging the observation target by use of the illumination light beams by a processor;
a step of generating a first image serving as a base of a display image to be displayed on a display unit, using any of the images acquired, by the processor;
a step of generating a plurality of second images, using at least one image having a different corresponding wavelength from that of the image used for the generation of the first image among the images acquired, by the processor, the processor generating the plurality of second images that are different from each other based on the images acquired for each of the illumination light beams and for each of the color filters;
a step of discriminating the regions in the observation target, using the plurality of second images, by the processor, the processor discriminating a different type of region for each of the second images; and
a step of generating the display image in which at least one region among the regions discriminated is enhanced, using the first image, by the processor,
wherein in a case where the processor discriminates a plurality of regions, the processor generates the display image by changing an enhancement method for every region discriminated, by changing a type of processing to be performed for each discriminated region or changing an importance of the processing for each discriminated region.

* * * * *